United States Patent
Franklin, Sr.

(10) Patent No.: US 10,595,873 B2
(45) Date of Patent: Mar. 24, 2020

(54) SURGICAL STAPLERS AND RELATED METHODS

(71) Applicant: Franklin Institute of Innovation, LLC, Peachtree City, GA (US)

(72) Inventor: James S. Franklin, Sr., Peachtree City, GA (US)

(73) Assignee: Franklin Institute of Innovation, LLC, Peachtree City, GA (US)

( * ) Notice: Subject to any disclaimer, the term of this patent is extended or adjusted under 35 U.S.C. 154(b) by 0 days.

(21) Appl. No.: 16/263,300

(22) Filed: Jan. 31, 2019

(65) Prior Publication Data

US 2019/0321044 A1 Oct. 24, 2019

Related U.S. Application Data

(60) Provisional application No. 62/659,899, filed on Apr. 19, 2018.

(51) Int. Cl.
*A61B 17/115* (2006.01)
*A61B 17/068* (2006.01)
*A61B 17/072* (2006.01)

(52) U.S. Cl.
CPC ........ *A61B 17/1155* (2013.01); *A61B 17/068* (2013.01); *A61B 2017/07257* (2013.01); *A61B 2017/1157* (2013.01)

(58) Field of Classification Search
CPC .............. A61B 17/1155; A61B 17/068; A61B 2017/07257; A61B 2017/1157
USPC ........... 227/175.1–182.1; 606/139, 142, 143, 606/205, 208
See application file for complete search history.

(56) References Cited

U.S. PATENT DOCUMENTS

| | | | | |
|---|---|---|---|---|
| 4,505,414 A | * | 3/1985 | Filipi | A61B 17/115 227/155 |
| 5,258,000 A | * | 11/1993 | Gianturco | A61B 17/0057 606/151 |
| 5,392,979 A | | 2/1995 | Green et al. | |
| 5,404,870 A | * | 4/1995 | Brinkerhoff | A61B 17/00 227/175.1 |
| 5,474,223 A | | 12/1995 | Viola et al. | |
| 5,478,319 A | | 12/1995 | Campbell et al. | |
| 5,478,320 A | * | 12/1995 | Trotta | A61M 25/10 604/103.06 |
| 5,522,534 A | | 6/1996 | Viola et al. | |

(Continued)

FOREIGN PATENT DOCUMENTS

WO 2010/087774 A1 8/2010

OTHER PUBLICATIONS

US 5,826,777 A, 10/1998, Green et al. (withdrawn)
International Search Report and Written Opinion, PCT/US2019/028272, 16 pages, dated Jul. 15, 2019.

*Primary Examiner* — Robert F Long
(74) *Attorney, Agent, or Firm* — Eversheds Sutherland (US) LLP

(57) ABSTRACT

Surgical staplers and methods of their use are provided. In one embodiment, a surgical stapler includes a tubular shaft having a proximal end and a distal end, a handle extending from the proximal end of the tubular shaft, a head assembly extending from the distal end of the tubular shaft, and an insertion guide configured to extend through the head assembly. The insertion guide includes an expandable member configured to move between a collapsed configuration and an expanded configuration.

18 Claims, 9 Drawing Sheets

(56) References Cited

U.S. PATENT DOCUMENTS

| | | | |
|---|---|---|---|
| 5,588,579 A | 12/1996 | Schnut et al. | |
| 5,616,114 A * | 4/1997 | Thornton | A61N 5/1002 600/3 |
| 5,758,814 A | 6/1998 | Gallagher et al. | |
| 5,766,158 A * | 6/1998 | Opolski | A61L 29/085 427/2.1 |
| 5,779,731 A * | 7/1998 | Leavitt | A61M 25/0108 604/103.1 |
| 5,799,857 A | 9/1998 | Robertson et al. | |
| 5,836,503 A | 11/1998 | Ehrenfels et al. | |
| 5,843,027 A * | 12/1998 | Stone | A61F 2/958 604/509 |
| 5,861,005 A * | 1/1999 | Kontos | A61B 17/0057 227/175.1 |
| 6,033,390 A | 3/2000 | Von Dyck | |
| 6,053,390 A | 4/2000 | Green et al. | |
| 6,066,132 A * | 5/2000 | Chen | A61B 18/08 604/530 |
| 6,102,271 A | 8/2000 | Longo et al. | |
| 6,174,318 B1 * | 1/2001 | Bates | A61B 17/221 606/113 |
| 6,254,642 B1 * | 7/2001 | Taylor | A61F 2/0004 623/2.1 |
| 6,279,809 B1 * | 8/2001 | Nicolo | A61B 17/068 227/176.1 |
| 6,338,737 B1 * | 1/2002 | Toledano | A61B 17/115 227/175.1 |
| 6,520,398 B2 | 2/2003 | Nicolo | |
| 6,957,758 B2 | 10/2005 | Aranyi | |
| 6,966,889 B2 | 11/2005 | Saab | |
| 7,168,604 B2 | 1/2007 | Milliman et al. | |
| 7,234,624 B2 | 6/2007 | Gresham et al. | |
| 7,261,722 B2 | 8/2007 | McGuckin | |
| 7,303,106 B2 | 12/2007 | Milliman et al. | |
| 7,325,713 B2 | 2/2008 | Aranyi | |
| 7,398,907 B2 | 7/2008 | Racenet et al. | |
| 7,401,722 B2 * | 7/2008 | Hur | A61B 17/115 227/179.1 |
| 7,451,765 B2 * | 11/2008 | Adler | A61B 17/12104 128/200.26 |
| 7,481,800 B2 | 1/2009 | Jacques | |
| 7,494,038 B2 | 2/2009 | Milliman | |
| 7,611,038 B2 | 11/2009 | Racenet et al. | |
| 7,824,426 B2 | 11/2010 | Racenet et al. | |
| 7,857,187 B2 | 12/2010 | Milliman | |
| 7,926,692 B2 | 4/2011 | Racenet et al. | |
| 8,109,962 B2 * | 2/2012 | Pal | A61F 2/013 606/200 |
| 8,123,101 B2 | 2/2012 | Racenet et al. | |
| 8,123,795 B1 * | 2/2012 | Knodel | A61B 17/068 623/1.11 |
| 8,353,438 B2 | 1/2013 | Baxter, III et al. | |
| 8,353,439 B2 | 1/2013 | Baxter, III et al. | |
| D680,646 S | 4/2013 | Hunt et al. | |
| D681,202 S | 4/2013 | Hunt et al. | |
| D685,472 S | 7/2013 | Hunt et al. | |
| 8,623,035 B1 | 1/2014 | Henderson | |
| 8,757,466 B2 * | 6/2014 | Olson | A61B 17/07207 227/178.1 |
| 8,827,903 B2 * | 9/2014 | Shelton, IV | A61B 17/072 600/217 |
| 9,451,962 B2 | 9/2016 | Olson | |
| 9,642,642 B2 * | 5/2017 | Lim | A61B 17/07207 |
| 2001/0041899 A1 * | 11/2001 | Foster | A61B 17/221 606/127 |
| 2003/0014064 A1 | 1/2003 | Blatter | |
| 2003/0183671 A1 * | 10/2003 | Mooradian | A61B 17/115 227/175.1 |
| 2003/0195405 A1 * | 10/2003 | Marino | A61B 5/04012 600/373 |
| 2003/0225419 A1 * | 12/2003 | Lippitt | A61B 17/221 606/127 |
| 2005/0051597 A1 * | 3/2005 | Toledano | A61B 17/115 227/176.1 |
| 2005/0130100 A1 * | 6/2005 | Wade | A61C 1/16 433/125 |
| 2005/0143756 A1 * | 6/2005 | Jankowski | A61B 17/115 606/139 |
| 2005/0145675 A1 * | 7/2005 | Hartwick | A61B 17/00234 227/180.1 |
| 2005/0187576 A1 * | 8/2005 | Whitman | A61B 17/1155 606/219 |
| 2005/0187616 A1 * | 8/2005 | Realyvasquez | A61B 17/11 623/2.11 |
| 2005/0274768 A1 * | 12/2005 | Cummins | A61B 17/0057 227/175.1 |
| 2006/0015136 A1 * | 1/2006 | Besselink | A61F 2/013 606/200 |
| 2006/0201989 A1 * | 9/2006 | Ojeda | A61B 17/11 227/175.1 |
| 2009/0114233 A1 * | 5/2009 | Edoga | A61B 17/068 128/898 |
| 2009/0204108 A1 * | 8/2009 | Steffen | A61B 17/068 606/1 |
| 2009/0264914 A1 * | 10/2009 | Riina | A61B 17/12113 606/191 |
| 2010/0010303 A1 * | 1/2010 | Bakos | A61B 1/00082 600/115 |
| 2010/0163598 A1 * | 7/2010 | Belzer | A61B 17/115 227/181.1 |
| 2010/0249805 A1 * | 9/2010 | Olson | A61B 17/07207 606/144 |
| 2011/0017802 A1 * | 1/2011 | Ma | A61B 17/07207 227/176.1 |
| 2011/0066231 A1 * | 3/2011 | Cartledge | A61B 17/068 623/2.11 |
| 2011/0118761 A1 * | 5/2011 | Baxter, III | A61B 46/10 606/148 |
| 2011/0230897 A1 * | 9/2011 | Palermo | A61B 17/0057 606/142 |
| 2011/0245854 A1 * | 10/2011 | Buxbaum | A61B 17/068 606/153 |
| 2011/0248067 A1 * | 10/2011 | Takei | A61B 17/115 227/175.1 |
| 2014/0224686 A1 * | 8/2014 | Aronhalt | A61B 17/068 206/339 |
| 2014/0252062 A1 * | 9/2014 | Mozdzierz | A61B 17/07292 227/175.1 |
| 2015/0173757 A1 * | 6/2015 | Williams | A61B 17/1155 227/180.1 |
| 2015/0351621 A1 | 12/2015 | Hill | |
| 2016/0324525 A1 * | 11/2016 | Scheib | A61B 17/1155 |
| 2017/0281181 A1 * | 10/2017 | Matonick | A61B 17/07292 |
| 2017/0325817 A1 * | 11/2017 | Racenet | A61B 17/1155 |
| 2018/0242975 A1 * | 8/2018 | Penna | A61B 46/13 |
| 2019/0343521 A1 * | 11/2019 | Williams | A61B 17/07292 |

\* cited by examiner

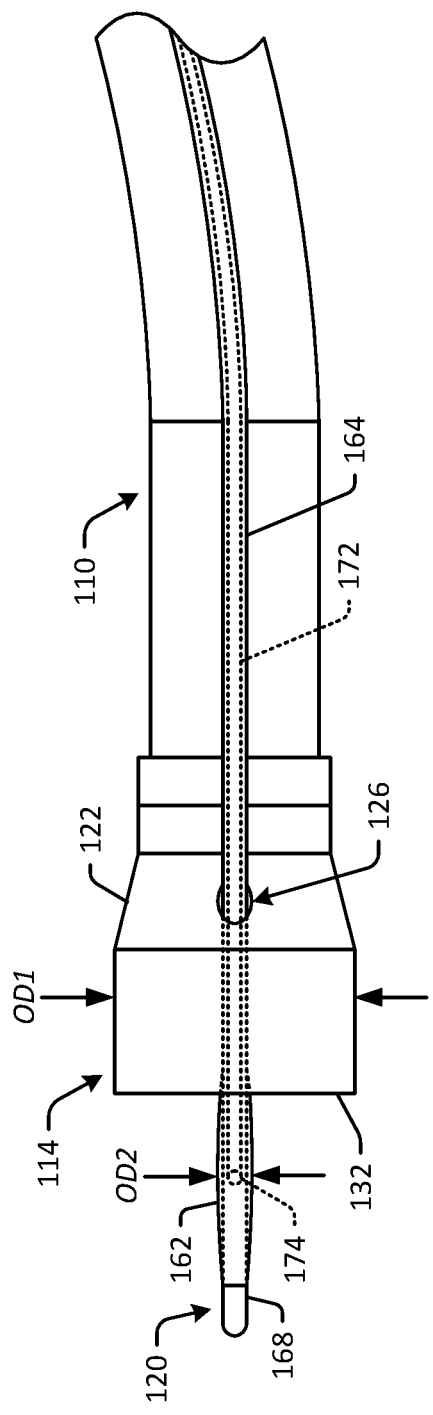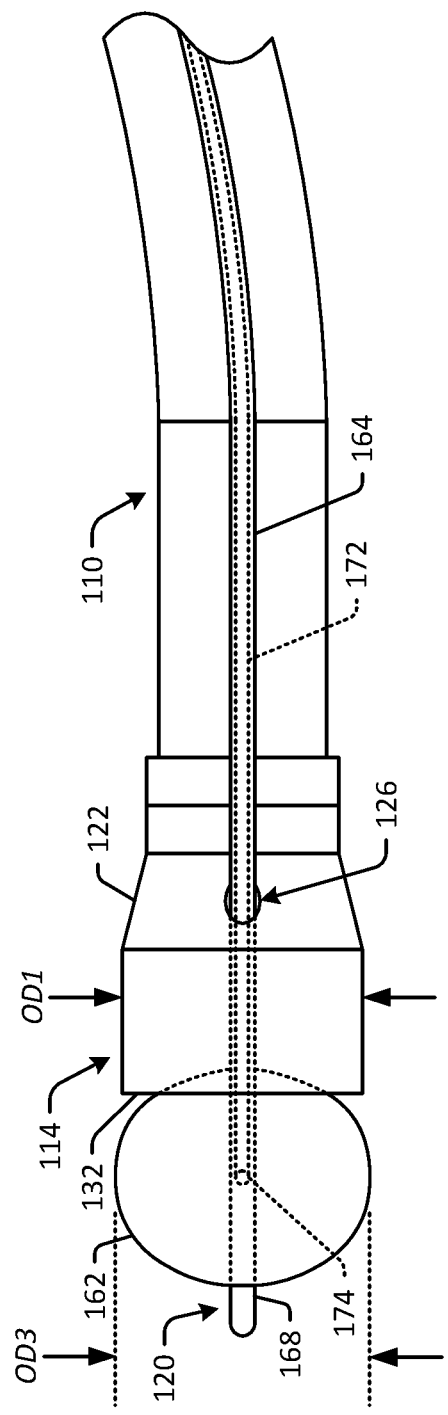

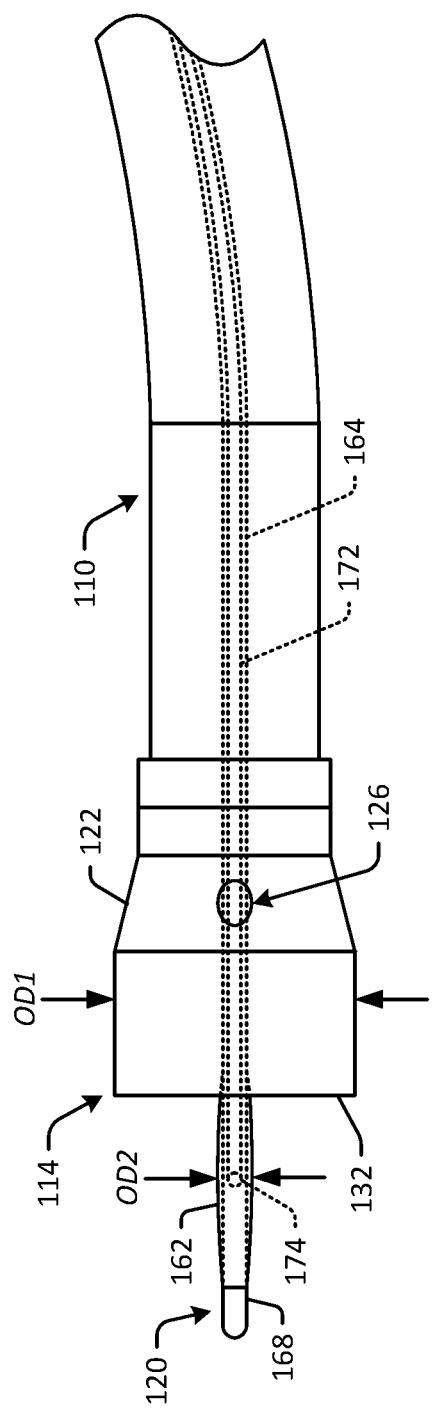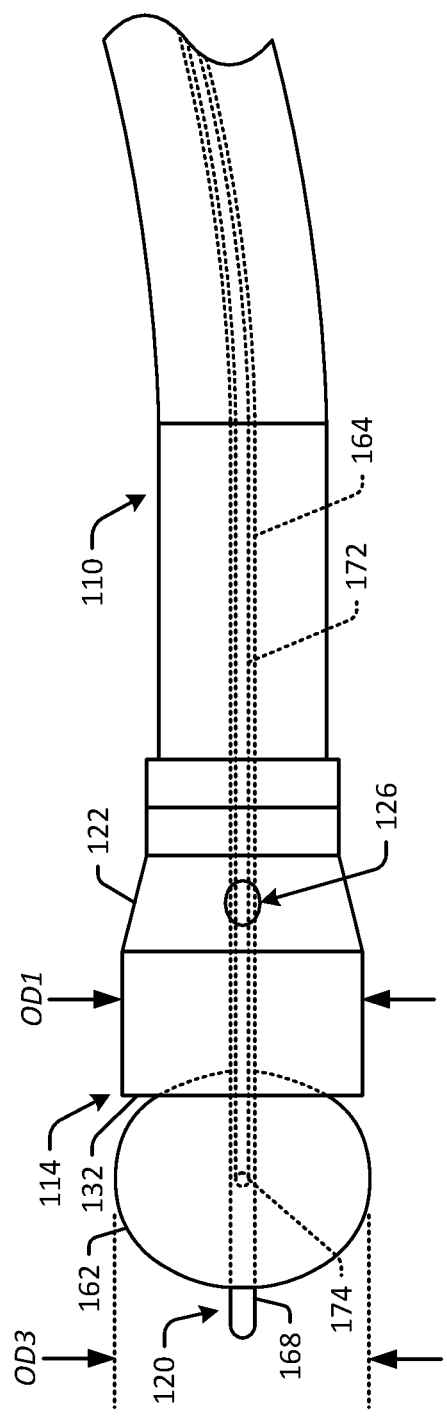

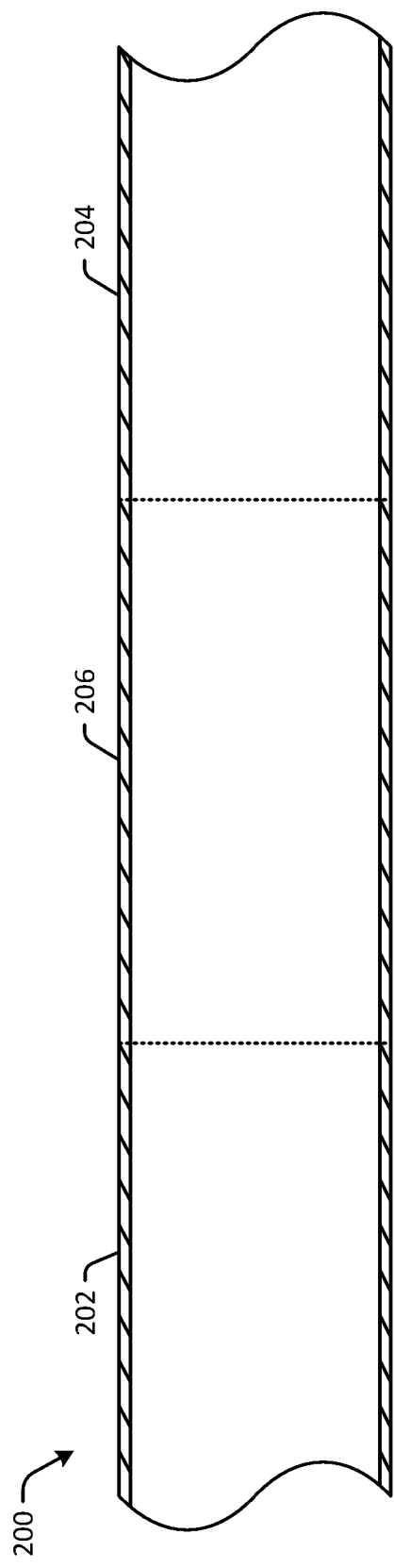
FIG. 2A
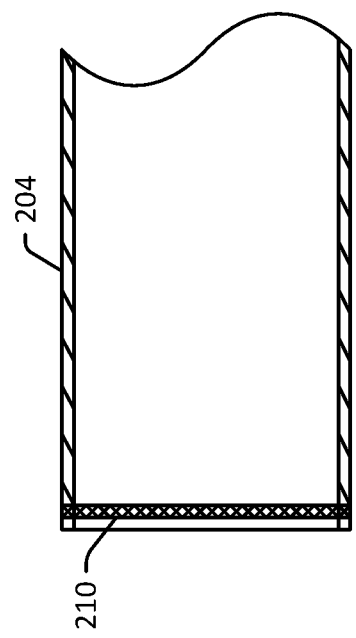
FIG. 2B
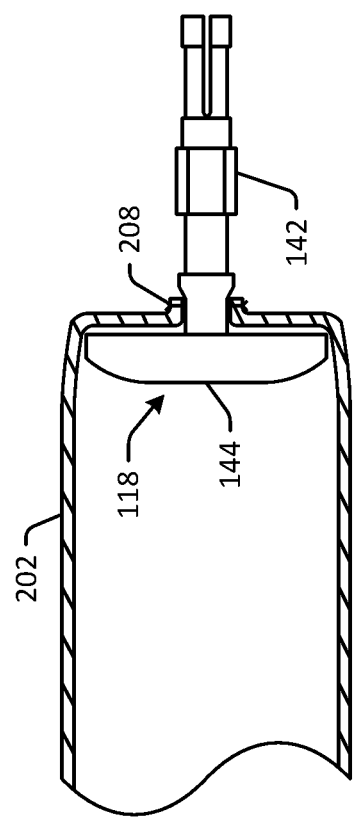

SURGICAL STAPLERS AND RELATED METHODS

CROSS-REFERENCE TO RELATED APPLICATIONS

This application claims the benefit of U.S. Provisional Application No. 62/659,899, filed on Apr. 19, 2018, which is incorporated by reference herein in its entirety.

TECHNICAL FIELD

The present disclosure relates generally to surgical instruments and methods, and more particularly to surgical staplers and related methods of using such staplers to perform an end-to-end anastomosis between two tubular tissue segments.

BACKGROUND

Various types of surgical procedures may necessitate anastomosis between two tubular tissue segments in order to restore the natural function of the tissue segments. For example, during colon and rectal resection surgery, a diseased or otherwise defective portion of the colon of a patient may be removed, and the colon segments above and below the removed portion may need to be reconnected to restore the natural flow through the colon. Traditionally, the upper and lower colon segments were rejoined by suturing the respective ends of the colon segments to one another. In recent years, surgical staplers have been developed for performing an end-to-end anastomosis between two tubular tissue segments, allowing clinicians to reconnect the tissue segments in a more efficient and reliable manner during a surgical procedure.

Existing surgical staplers for performing an end-to-end anastomosis generally may include an elongated tubular shaft, a handle attached to a proximal end of the tubular shaft, and a head assembly attached to a distal end of the tubular shaft. The head assembly may include an outer shell that contains a mechanism for forming a circular array of staples to connect two tubular tissue segments. For example, a staple guide may be fixedly positioned within the outer shell along a distal end thereof, and a staple pusher may be movably positioned within the outer shell and configured for advancing a plurality of staples through the staple guide. The head assembly also may include a mechanism for coring respective portions of the tissue segments being stapled to one another. For example, a circular knife may be movably positioned within the outer shell and configured for cutting inner portions of the tissue segments within the circular array of staples. The formation of the array of staples and the removal of the inner portions of the tissue segments may be facilitated by an anvil that is removably attached to a trocar of the head assembly. The trocar may be movably positioned within the outer shell and configured to draw an anvil head of the anvil adjacent to the distal end of the outer shell. In this manner, the staples may be advanced through the staple guide, through respective portions of the tissue segments, and against the anvil head to facilitate desired deformation of the staples. Additionally, the circular knife may be advanced through respective portions of the tissue segments and against the anvil head to cut and remove inner portions of the tissue segments within the circular array of staples.

When existing surgical staplers are used to perform an end-to-end anastomosis between two colon segments, the head assembly and a portion of the tubular shaft of the stapler may be inserted through the anus of the patient and advanced through the rectum to the end of the lower color segment, while the handle remains outside of the patient to allow the clinician to control positioning and operation of the stapler. The head assembly generally may be relatively large in order to accommodate the various components for staple formation and for cutting the inner portions of the colon segments being joined. Further, the distal end face of the head assembly may be flat or relatively flat in order to cooperate with the mating portion of the anvil head, resulting in an abrupt edge along the outer circumference of the head assembly. In many instances, it may be challenging for the clinician to insert the head assembly through the anus and the rectum and advance the head assembly to the desired location at the end of the lower colon segment. For example, due to the size and/or shape of the head assembly, it may be difficult to advance the head assembly through the anus and then through the contours of the rectum without snagging on the mucosa folds. In some instances, as the head assembly is advanced to the desired location, the size and/or shape of the head assembly may result in injury to the surrounding anatomy and various complications for the patient. For example, introduction of the head assembly may result in anal sphincter injury, which may lead to loss of voluntary control of bowel function. Additionally, as the head assembly is moved to the desired location, it may engage and cause damage to the internal lining of the colon, which may lead to bleeding or potentially a leak along the respective region of the colon. Finally, in view of the known challenges in advancing the head assembly to the desired location, clinicians often may remove a larger portion of the colon than is truly needed in order to ease insertion and positioning of the head assembly within the patient.

There remains a need for improved surgical staplers and methods of using such staplers to perform an end-to-end anastomosis between two tubular tissue segments, such as colon segments following resection of a portion of the colon. In particular, it would be advantageous to provide a surgical stapler that eases insertion and advancement of a head assembly of the stapler to a desired location for performing the anastomosis, while reducing incidence of injury to the surrounding anatomy and complications for the patient.

BRIEF SUMMARY

Surgical staplers and methods of using such staplers to perform an end-to-end anastomosis between two tubular tissue segments are provided. According to one aspect, a surgical stapler is provided. In one embodiment, the surgical stapler includes a tubular shaft having a proximal end and a distal end, a handle extending from the proximal end of the tubular shaft, a head assembly extending from the distal end of the tubular shaft, and an insertion guide configured to extend through the head assembly. The insertion guide includes an expandable member configured to move between a collapsed configuration and an expanded configuration.

In some embodiments, the head assembly includes a distal end face, and the insertion guide is configured to extend distally beyond the distal end face of the head assembly. In some embodiments, the expandable member is configured to engage the distal end face of the head assembly when the expandable member is in the expanded configuration. In some embodiments, the expandable member is configured to be spaced apart from the distal end face of the head assembly when the expandable member is in the collapsed configuration. In some embodiments, the head assembly includes an outer shell including a central bore defined therein, and the insertion guide is configured to extend at least partially through the central bore. In some embodiments, the central bore has a proximal end and a distal end, and the insertion guide is configured to extend through the distal end of the central bore. In some embodiments, the outer shell also includes a lateral opening defined in an outer surface of the outer shell and in communication with the central bore, and the insertion guide is configured to extend through the lateral opening and into the central bore. In some embodiments, the insertion guide is configured to be inserted through the lateral opening and into the central bore when the expandable member is in the collapsed configuration. In some embodiments, the head assembly also includes a staple guide positioned within the central bore, and the insertion guide is configured to extend through a central aperture of the staple guide. In some embodiments, the head assembly also includes a circular knife positioned within the central bore, and the insertion guide is configured to extend through a central aperture of the circular knife. In some embodiments, the expandable member is configured to be positioned at least partially within the central bore when the expandable member is in the expanded configuration. In some embodiments, the expandable member is configured to be withdrawn from the central bore when the expandable member is in the collapsed configuration.

In some embodiments, the head assembly has a first outer diameter, the expandable member has a second outer diameter when the expandable member is in the collapsed configuration, and the second outer diameter is less than the first outer diameter. In some embodiments, the expandable member has a third outer diameter when the expandable member is in the expanded configuration, and the third outer diameter is equal to or greater than the first outer diameter. In some embodiments, the expandable member includes a balloon configured to radially expand and collapse to move the expandable member between the collapsed configuration and the expanded configuration. In some embodiments, the balloon is formed of an elastomeric material. In some embodiments, the balloon has a curved outer surface when the expandable member is in the expanded configuration. In some embodiments, the insertion guide also includes a tube extending from a proximal end of the expandable member and in fluid communication with an internal reservoir of the balloon. In some embodiments, the insertion guide also includes a port attached to a proximal end of the tube and configured to attach to a fluid delivery device. In some embodiments, the insertion guide is configured to extend through the tubular shaft and the head assembly.

In another embodiment, the surgical stapler includes a tubular shaft having a proximal end and a distal end, a handle extending from the proximal end of the tubular shaft, a head assembly extending from the distal end of the tubular shaft, and an insertion guide. The head assembly includes a distal end face and a central bore defined therein. The insertion guide is configured to be positioned at least partially within the central bore. The insertion guide includes an expandable member configured to move between a collapsed configuration and an expanded configuration. The expandable member is configured to be spaced apart from the distal end face when the expandable member is in the collapsed configuration, and the expandable member is configured to engage the distal end face when the expandable member is in the expanded configuration.

In some embodiments, the expandable member is configured to be positioned at least partially within the central bore when the expandable member is in the expanded configuration. In some embodiments, the head assembly has a first outer diameter, the expandable member has a second outer diameter when the expandable member is in the collapsed configuration, and the second outer diameter is less than the first outer diameter. In some embodiments, the expandable member has a third outer diameter when the expandable member is in the expanded configuration, and the third outer diameter is equal to or greater than the first outer diameter. In some embodiments, the head assembly also includes a lateral opening defined in an outer surface of the head assembly and in communication with the central bore, and the insertion guide is configured to extend through the lateral opening and into the central bore. In some embodiments, the head assembly also includes a staple guide positioned within the central bore, and the insertion guide is configured to extend through a central aperture of the staple guide. In some embodiments, the head assembly also includes a circular knife positioned within the central bore, and the insertion guide is configured to extend through a central aperture of the circular knife. In some embodiments, the expandable member includes a balloon configured to radially expand and collapse to move the expandable member between the collapsed configuration and the expanded configuration. In some embodiments, the insertion guide is configured to extend through the tubular shaft and the head assembly.

In still another embodiment, the surgical stapler includes a tubular shaft having a proximal end and a distal end, a handle extending from the proximal end of the tubular shaft, a head assembly extending from the distal end of the tubular shaft, and an insertion guide configured to extend through the head assembly. The insertion guide includes a balloon and a tube. The balloon is configured to move between a collapsed configuration and an expanded configuration. The tube extends from a proximal end of the balloon and is in fluid communication with an internal reservoir of the balloon.

In some embodiments, the head assembly includes a distal end face, and the insertion guide is configured to extend distally beyond the distal end face. In some embodiments, In some embodiments, the balloon is configured to be spaced apart from the distal end face when the balloon is in the collapsed configuration, and the balloon is configured to engage the distal end face when the balloon is in the expanded configuration. In some embodiments, the head assembly comprises a central bore defined therein, and the insertion guide is configured to extend at least partially through the central bore. In some embodiments, the balloon is configured to be positioned at least partially within the central bore when the balloon is in the expanded configuration. In some embodiments, the head assembly also includes a lateral opening defined in an outer surface of the head assembly and in communication with the central bore, and the insertion guide is configured to extend through the lateral opening and into the central bore. In some embodiments, the head assembly also includes a staple guide and a circular knife positioned within the central bore, and the insertion guide is configured to extend through a central aperture of the staple guide and a central aperture of the circular knife. In some embodiments, the head assembly has a first outer diameter, the balloon has a second outer diameter when the balloon is in the collapsed configuration, and the second outer diameter is less than the first outer diameter. In some embodiments, the balloon has a third outer diameter when the balloon is in the expanded configuration, and the third outer diameter is equal to or greater than the first outer diameter. In some embodiments, the insertion guide is configured to extend through the tubular shaft and the head assembly.

In another aspect, a method of introducing a surgical stapler into a patient is provided. In one embodiment, the method includes the steps of advancing an insertion guide through a head assembly of the surgical stapler, such that the insertion guide extends distally beyond a distal end face of the head assembly, moving an expandable member of the insertion guide from a collapsed configuration to an expanded configuration, and inserting the expandable member and the head assembly into a tubular tissue structure of the patient while the expandable member is in the expanded configuration.

In some embodiments, the surgical stapler also includes a tubular shaft extending from a proximal end of the head assembly, and the method also includes advancing the insertion guide through the tubular shaft. In some embodiments, advancing the insertion guide through the head assembly includes advancing the expandable member through the head assembly while the expandable member is in the collapsed configuration. In some embodiments, the head assembly includes a central bore defined therein and a lateral opening defined in an outer surface of the head assembly and in communication with the central bore, and advancing the insertion guide through the head assembly includes advancing the expandable member through the lateral opening and at least partially through the central bore. In some embodiments, moving the expandable member from the collapsed configuration to the expanded configuration comprises engaging the distal end face with the expandable member. In some embodiments, the expandable member includes a balloon, and moving the expandable member from the collapsed configuration to the expanded configuration includes inflating the balloon. In some embodiments, the insertion guide also includes a tube extending from a proximal end of the balloon and in fluid communication with an internal reservoir of the balloon, and inflating the balloon includes delivering a fluid through the tube and into the internal reservoir.

In some embodiments, the head assembly has a first outer diameter, the expandable member has a second outer diameter when the expandable member is in the collapsed configuration, the expandable member has a third outer diameter when the expandable member is in the expanded configuration, the second outer diameter is less than the first outer diameter, and the third outer diameter is equal to or greater than the first outer diameter. In some embodiments, the method also includes the steps of advancing the expandable member and the head assembly through the tubular tissue structure to a target location, moving the expandable member from the expanded configuration to the collapsed configuration while the expandable member is at the target location, and removing the insertion guide from the head assembly. In some embodiments, the tubular tissue structure includes a segment of a colon of the patient.

In still another aspect, a method of using a surgical stapler to perform an end-to-end anastomosis between a first tubular tissue segment and a second tubular tissue segment of a patient is provided. In one embodiment, the method includes the steps of inserting an anvil of the surgical stapler at least partially into the first tubular tissue segment, advancing an insertion guide through a head assembly of the surgical stapler, such that the insertion guide extends distally beyond a distal end face of the head assembly, moving an expandable member of the insertion guide from a collapsed configuration to an expanded configuration, inserting the expandable member and the head assembly into the patient while the expandable member is in the expanded configuration, advancing the expandable member and the head assembly through the second tubular tissue segment to a target location adjacent an end of the second tubular tissue segment, moving the expandable member from the expanded configuration to the collapsed configuration while the expandable member is at the target location, removing the insertion guide from the head assembly, advancing a trocar of the surgical stapler through the end of the second tubular tissue segment, attaching the anvil to the trocar, and connecting the first tubular tissue segment to the second tubular tissue segment via a plurality of staples.

In some embodiments, the surgical stapler also includes a tubular shaft extending from a proximal end of the head assembly, and the method also includes advancing the insertion guide through the tubular shaft. In some embodiments, advancing the insertion guide through the head assembly includes advancing the expandable member through the head assembly while the expandable member is in the collapsed configuration. In some embodiments, the head assembly includes a central bore defined therein and a lateral opening defined in an outer surface of the head assembly and in communication with the central bore, and advancing the insertion guide through the head assembly comprises advancing the expandable member through the lateral opening and at least partially through the central bore. In some embodiments, moving the expandable member from the collapsed configuration to the expanded configuration includes engaging the distal end face with the expandable member. In some embodiments, the expandable member includes a balloon, and moving the expandable member from the collapsed configuration to the expanded configuration comprises inflating the balloon. In some embodiments, the insertion guide also includes a tube extending from a proximal end of the balloon and in fluid communication with an internal reservoir of the balloon, and inflating the balloon includes delivering a fluid through the tube and into the internal reservoir.

In some embodiments, the head assembly has a first outer diameter, the expandable member has a second outer diameter when the expandable member is in the collapsed configuration, the expandable member has a third outer diameter when the expandable member is in the expanded configuration, the second outer diameter is less than the first outer diameter, and the third outer diameter is equal to or greater than the first outer diameter. In some embodiments, the first tubular tissue segment includes an upper colon segment, the second tubular tissue segment includes a lower colon segment, and inserting the expandable member and the head assembly into the patient includes inserting the expandable member and the head assembly through an anus of the patient while the expandable member is in the expanded configuration. In some embodiments, the method also includes advancing the expandable member and the head assembly through a rectum of the patient while the expandable member is in the expanded configuration.

These and other aspects and embodiments of the present disclosure will be apparent or will become apparent to one of ordinary skill in the art upon review of the following detailed description when taken in conjunction with the drawings and the appended claims.

BRIEF DESCRIPTION OF THE DRAWINGS

FIG. 1F is a detailed side view of a portion of the surgical stapler of FIG. 1A, showing the insertion guide extending through the head assembly, with an expandable member of the insertion guide in a collapsed configuration.

FIG. 1G is a detailed side view of a portion of the surgical stapler of FIG. 1A, showing the insertion guide extending through the head assembly, with the expandable member in an expanded configuration.

FIG. 1H is a detailed side view of a portion of the surgical stapler of FIG. 1A, showing the insertion guide extending through the tubular shaft and the head assembly, with an expandable member of the insertion guide in a collapsed configuration.

FIG. 1I is a detailed side view of a portion of the surgical stapler of FIG. 1A, showing the insertion guide extending through the tubular shaft and the head assembly, with the expandable member in an expanded configuration.

FIGS. 2A-2H illustrate a method of using the surgical stapler of FIG. 1A to perform an end-to-end anastomosis between two tissue segments of a tubular tissue structure in accordance with one or more embodiments of the disclosure FIG. 2A is a cross-sectional side view of the tubular tissue structure, showing a portion of the tubular tissue structure to be removed.

FIG. 2B is a partial cross-sectional side view of a first tissue segment and a second tissue segment of the tubular tissue structure, showing the anvil of the surgical stapler of FIG. 1A positioned partially within and extending from the first tissue segment.

FIG. 2C is a partial cross-sectional side view of the first tissue segment and the second tissue segment, showing the expandable member of the surgical stapler of FIG. 1A in the expanded configuration and positioned within the second tissue segment adjacent a closed end thereof.

FIG. 2D is a partial cross-sectional side view of the first tissue segment and the second tissue segment, showing the head assembly of the surgical stapler of FIG. 1A positioned adjacent the closed end of the second tissue segment, with the trocar in the retracted position.

FIG. 2E is a partial cross-sectional side view of the first tissue segment and the second tissue segment, showing the head assembly positioned adjacent the closed end of the second tissue segment, with the trocar in the extended position and extending through the closed end of the second tissue segment.

FIG. 2F is a partial cross-sectional side view of the first tissue segment and the second tissue segment, showing the trocar in the extended position and attached to the anvil.

FIG. 2G is a partial cross-sectional side view of the first tissue segment and the second tissue segment, showing the trocar in the retracted position and attached to the anvil.

FIG. 2H is a cross-sectional side view of the first tissue segment and the second tissue segment, showing the first tissue segment and the second tissue segment joined to one another by a circular array of staples.

DETAILED DESCRIPTION

Improved surgical staplers and methods have been developed for performing an end-to-end anastomosis between two tubular tissue segments, such as colon segments following resection of a portion of the colon. Such surgical staplers and methods advantageously may ease insertion and advancement of a head assembly of a stapler to a desired location for performing an anastomosis, while reducing incidence of injury to the surrounding anatomy and corresponding complications for the patient. In particular, the surgical staplers described herein may include an insertion guide having an atraumatic expandable member, such as a balloon, that is configured to be positioned about a distal end of the head assembly. The expandable member may be moved, or transitioned, from a collapsed configuration to an expanded configuration prior to introduction of the stapler into the patient. While in the expanded configuration, the expandable member may cover a distal end face of the head assembly, thereby inhibiting the distal end face from engaging the surrounding anatomy as the head assembly is advanced toward a desired location within a tissue segment. Once the expandable member reaches the desired location, the expandable member may be moved, or transitioned, from the expanded configuration to the collapsed configuration, and the insertion guide may be withdrawn from the head assembly and removed from the patient.

As compared to existing staplers for performing an end-to-end anastomosis, the surgical staplers described herein may allow clinicians to more easily and efficiently introduce a stapler into a patient in a manner that inhibits injury to the surrounding anatomy. For example, in the context of rejoining an upper colon segment and a lower colon segment following resection of a portion of the colon, the atraumatic expandable member of the insertion guide may ease insertion of the head assembly through the anus and advancement of the head assembly through the rectum to the closed end of the lower colon segment. In particular, the expandable member may engage portions of the surrounding anatomy instead of the head assembly, and the curved shape and flexible nature of the expandable member may facilitate advancement of the head assembly through restricted regions and contours of the anatomy without causing injury to the patient. As a result, the surgical staplers described herein may reduce incidence of anal sphincter injury and/or damage to the internal lining of the colon, as may be experienced during use of existing surgical staplers. Further, the surgical staplers described herein may obviate the clinical practice of removing a larger portion of the colon than is needed for the purpose of easing insertion and positioning of the stapler.

Surgical Staplers

Figure 1A:
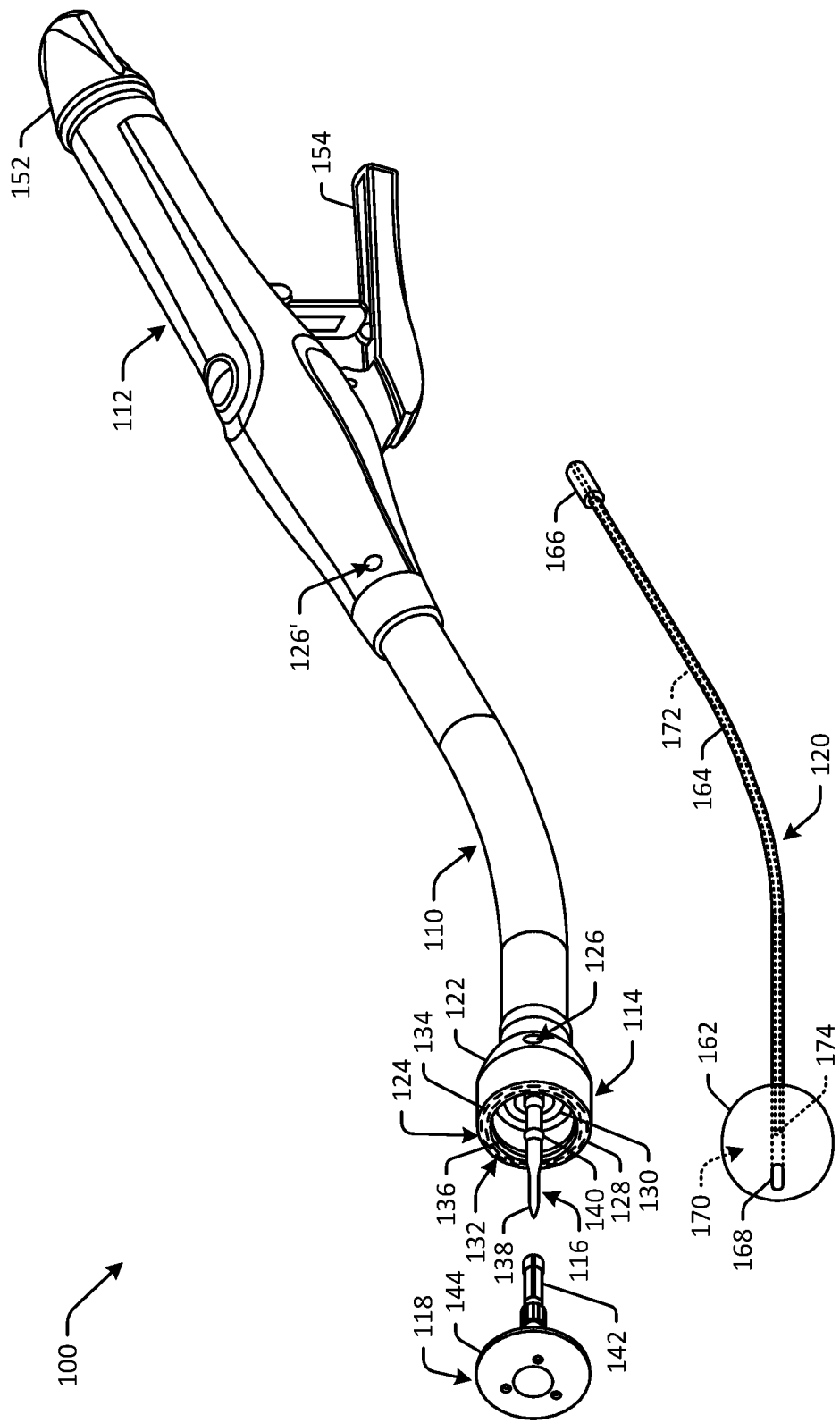
FIG. 1A is a perspective view of a surgical stapler in accordance with one or more embodiments of the disclosure, showing a tubular shaft, a handle, a head assembly, a trocar, an anvil, and an insertion guide of the surgical stapler.

FIGS. 1A-1G illustrate a surgical stapler 100 (which also may be referred to as an "circular stapler" or simply a "stapler") configured to perform an end-to-end anastomosis between two tubular tissue segments of a patient, in accordance with one or more embodiments of the disclosure. For example, the surgical stapler 100 may be used following resection of a portion of a patient's colon to reconnect upper and lower colon segments, as described below with respect to FIGS. 2A-2H. As shown in FIG. 1A, the surgical stapler 100 includes a tubular shaft 110, a handle 112, a head assembly 114, a trocar 116, an anvil 118, and an insertion guide 120. During use of the surgical stapler 100, the head assembly 114 and a portion of the tubular shaft 110 may be inserted into a patient, while the handle 112 remains outside of the patient to allow a clinician to control operation of the stapler 100. As described below, the insertion guide 120 may be used to facilitate insertion of the head assembly 114 into the patient and to guide advancement of the head assembly 114 to a target location for performing an anastomosis. Once the head assembly 114 is positioned at or near the target location, the insertion guide 120 may be removed from the patient, and the head assembly 114, the trocar 116, and the anvil 118 then may be used in a conventional manner to connect two tubular tissue segments via a circular array of staples.

The tubular shaft 110 may be formed as elongated hollow member having a proximal end and a distal end. As shown, the handle 112 may extend from the proximal end of the tubular shaft 110, and the head assembly 114 may extend from the distal end of the tubular shaft 110. In some embodiments, the handle 112 and the head assembly 114 may be fixedly attached to the tubular shaft 110. In other embodiments, the handle 112 and/or the head assembly 114 may be removably attached to the tubular shaft 110. As shown, the tubular shaft 110 may have a contoured shape including one or more curved regions and one or more straight regions. Alternatively, the tubular shaft 110 may have a straight shape extending from the proximal end to the distal end thereof. As described below, various internal components of the surgical stapler 100 may be positioned within or extend through the lumen of the tubular shaft 110 to allow components of the head assembly 114 to be controlled by the clinician from outside of the patient during use of the stapler 100. It will be appreciated that the illustrated tubular shaft 110 is merely one example embodiment, and that other shapes and configurations of the tubular shaft 110 may be used with the surgical stapler 100.

The handle 112 may be formed as an elongated member extending proximally from the proximal end of the tubular shaft 110. As shown, the handle 112 may have a contoured shape to allow the clinician to easily grasp the handle 112 and move the surgical stapler 100 relative to the patient. In some embodiments, a portion or all of the handle 112 may be formed as a hollow member defining an interior space for containing various internal components of the surgical stapler 100 therein. It will be appreciated that the illustrated handle 112 is merely one example embodiment, and that other shapes and configurations of the handle 112 may be used with the surgical stapler 100.

The head assembly 114 may be formed as an elongated assembly extending distally from the distal end of the tubular shaft 110. As shown, the head assembly 114 may include an outer shell 122 that is attached to a distal end portion of the tubular shaft 110 and configured to contain other components of the head assembly 114 therein. The outer shell 122 may be formed as a substantially hollow member including a central bore 124 defined therein. The central bore 124 may extend from a distal end toward a proximal end of the outer shell 122. In this manner, the central bore 124 may be in communication with the lumen of the tubular shaft 110 to allow various components of the surgical stapler 100 to extend through the tubular shaft 110 and the head assembly 114. As shown, the outer shell 122 also may include a lateral opening 126 that is defined in an outer surface of the outer shell 122 and in communication with the central bore 124. In other words, the lateral opening 126 may extend from the outer surface of the outer shell 122 to the central bore 124. As described below, the lateral opening 126 may allow the insertion guide 120 to pass through the lateral opening 126 and into the central bore 124 during use of the insertion guide 120.

The head assembly 114 may include one or more components to facilitate formation of a circular array of staples to connect two tubular tissue segments. For example, the head assembly 114 may include a staple guide 128 and a staple pusher 130. The staple guide 128 may be fixedly positioned within the central bore 124 of the outer shell 122. As shown, the staple guide 128 may extend to the distal end of the outer shell 122. In this manner, the distal end of the staple guide 128 and the distal end of the outer shell 122 may define a distal end face 132 of the head assembly 114. The distal end face 132 may be a planar or substantially planar surface extending transverse to, such as perpendicular to, the longitudinal axis of the head assembly 114. As shown, the staple guide 128 may be formed as a ring-shaped member having a plurality of slots 134 defined therein and a central aperture extending through the staple guide 128. The slots 134 may be arranged in a circular array, and each slot 134 may be configured to receive a respective staple therein. In this manner, the slots 134 of the staple guide 128 may maintain the plurality of staples in respective positions around the longitudinal axis of the head assembly 114 to facilitate formation of a circular array of staples for joining the tubular tissue segments. The staple pusher 130 may be movably positioned within the central bore 124 of the outer shell 122. For example, the staple pusher 130 may be configured to translate relative to the outer shell 122 along the longitudinal axis of the head assembly 114 between a retracted position and an extended position. As shown, the staple pusher 130 may be positioned axially between the staple guide 128 and the outer shell 122. The staple pusher 130 may include a base portion and a plurality of protrusions extending distally from the base portion and corresponding to the slots 134 of the staple guide 128. When the staple pusher 130 moves from the retracted position to the extended position, the protrusions of the staple pusher 130 may engage the respective slots 134 and cause the staples to be ejected therefrom. In some embodiments, the staple pusher 130 may include an aperture that is aligned with the lateral opening 126 of the outer shell 122 when the staple pusher 130 is in the retracted position. In this manner, the insertion guide 120 may pass through the lateral opening 126, through the aperture of the staple pusher 130, and into the central bore 124 during use of the insertion guide 120.

The head assembly 114 also may include one or more components for coring respective portions of the tubular tissue segments being connected to one another. For example, the head assembly 114 may include a circular knife 136. The circular knife 136 may be movably positioned within the central bore 124 of the outer shell 122. For example, the circular knife 136 may be configured to translate relative to the outer shell 122 along the longitudinal axis of the head assembly 114 between a retracted position and an extended position. The circular knife 136 may be formed as a tubular member having a cutting edge along the distal end of the circular knife 136 and a central aperture extending through the circular knife 136. In some embodiments, the circular knife 136 may be fixedly attached to the staple pusher 130. In this manner, the circular knife 136 may move along with the staple pusher 130 between the retracted position and the extended position. When the circular knife 136 is in the extended position, the cutting edge thereof may extend distally beyond the staple guide 128 to engage and cut radially inner portions of the tubular tissue segments. It will be appreciated that the illustrated head assembly 114 is merely one example embodiment, and that other shapes and configurations of the head assembly 114 may be used with the surgical stapler 100.

Figure 1B:
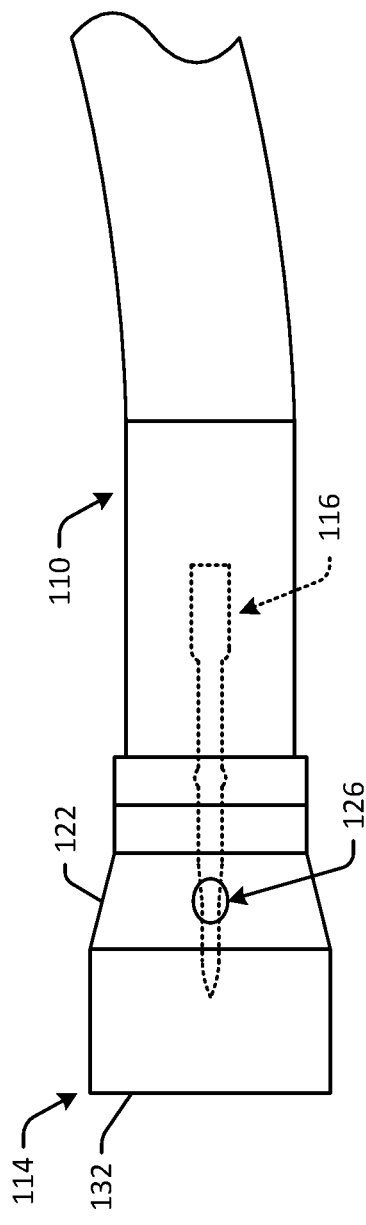
FIG. 1B is a detailed side view of a portion of the surgical stapler of FIG. 1A, showing the trocar in a retracted position.
Figure 1C:
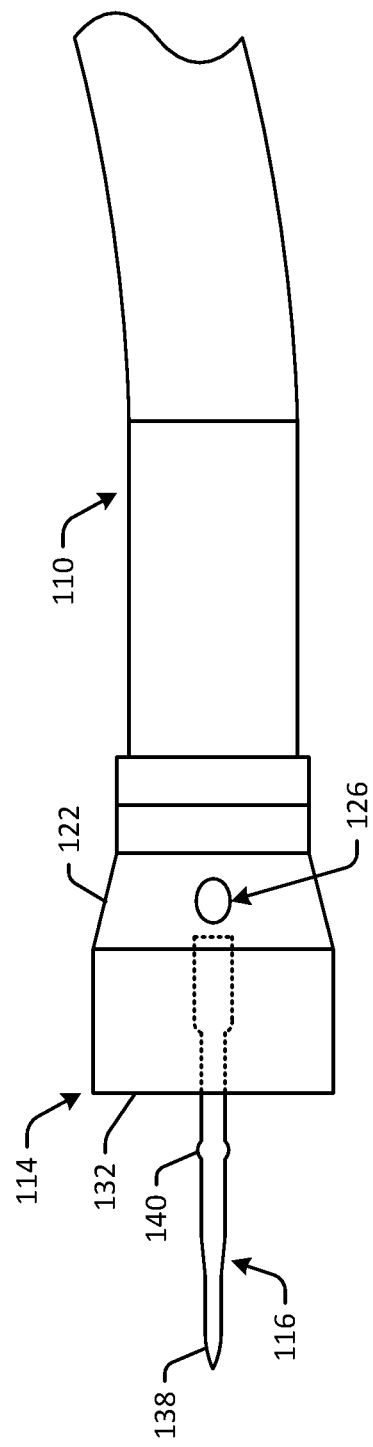
FIG. 1C is a detailed side view of a portion of the surgical stapler of FIG. 1A, showing the trocar in an extended position.

The trocar 116 may be formed as an elongated member extending along the longitudinal axis of the head assembly 114. The trocar 116 movably positioned within the tubular shaft 110 and/or the head assembly 114. For example, the trocar 116 may be configured to translate relative to the outer shell 122 along the longitudinal axis of the head assembly 114 between a retracted position, as shown in FIG. 1B, and an extended position, as shown in FIGS. 1A and 1C. When the trocar 116 is in the retracted position, a proximal portion of the trocar 116 may be positioned within the tubular shaft 110, and a distal portion of the trocar 116 may be positioned within the head assembly 114. When the trocar 116 is in the extended position, a proximal portion of the trocar 116 may be positioned within the head assembly 114, and a distal portion of the trocar 116 may extend distally beyond the distal end of the head assembly 114. As shown, the trocar 116 may include a distal tip 138 configured to penetrate tissue during use of the surgical stapler 100, as described below. The trocar 116 also may include a protrusion 140 extending along the outer circumference of an intermediate portion of the trocar 116 and configured to facilitate attachment of the anvil 118 to the trocar 116 during use of the surgical stapler 100. It will be appreciated that the illustrated trocar 116 is merely one example embodiment, and that other shapes and configurations of the trocar 116 may be used with the surgical stapler 100.

Figure 1D:
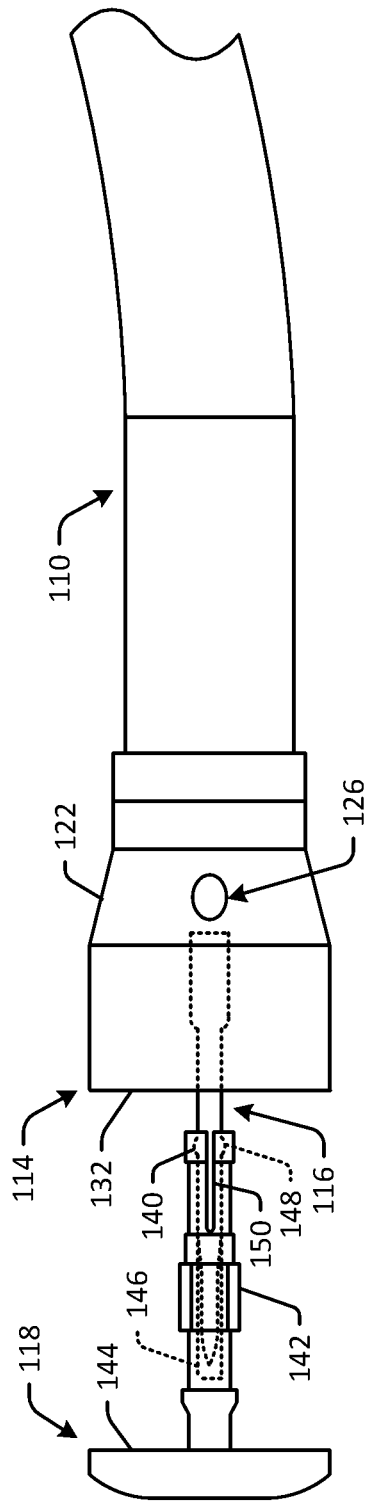
FIG. 1D is a detailed side view of a portion of the surgical stapler of FIG. 1A, showing the anvil attached to the trocar, with the trocar in the extended position.
Figure 1E:
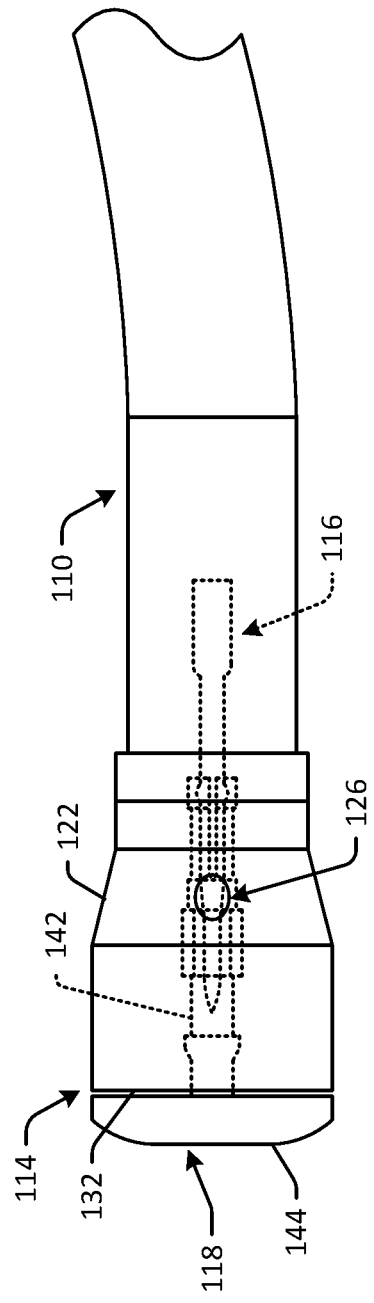
FIG. 1E is a detailed side view of a portion of the surgical stapler of FIG. 1A, showing the anvil attached to the trocar, with the trocar in the retracted position.

The anvil 118 may be formed as an elongated assembly configured for attachment to the trocar 116. As shown, the anvil 118 may include an anvil shaft 142 and an anvil head 144 attached to one another. In some embodiments, the anvil head 144 may be fixedly attached to the anvil shaft 142, with the anvil head 144 extending perpendicular to the longitudinal axis of the anvil shaft 142. In other embodiments, the anvil head 144 may be pivotably attached to the anvil shaft 142, such that the orientation of the anvil head 144 relative to the longitudinal axis of the anvil shaft 142 may be adjusted, for example, to ease insertion of the anvil head 144 into or removal of the anvil head 144 from a tubular tissue segment. The anvil shaft 142 may include a central passage 146 for receiving a distal portion of the trocar 116 therein, as shown in FIG. 1D. The anvil shaft 142 also may include a groove 148 extending along the inner circumference of the central passage 146 and configured to receive the protrusion 140 of the trocar 116 therein as well as one or more elongated slots 150 to facilitate a snap-fit connection between the anvil shaft 142 and the trocar 116. During use of the surgical stapler 100, the anvil 118 may be attached to the trocar 116 and then moved relative to the head assembly 114 from an extended position, as shown in FIG. 1D, to a retracted position, as shown in FIG. 1E. In this manner, the movement of the trocar 116 from its extended position to its retracted position may move the anvil 118 from its extended position to its retracted position. When the anvil 118 is in the retracted position, the anvil head 144 may be positioned adjacent to or near the distal end of the head assembly 114. In this manner, the anvil head 144 may facilitate desired deformation of the staples when the staples are ejected from the staple guide 128 and the free ends of the staples engage the anvil head 144. Additionally, the anvil head 144 may facilitate coring of the radially inner portions of the tissue segments when the circular knife 136 passes through the tissue segments and engages the anvil head 144. It will be appreciated that the illustrated anvil 118 is merely one example embodiment, and that other shapes and configurations of the anvil 118 may be used with the surgical stapler 100.

The surgical stapler 100 may include one or more components configured to allow the clinician to control movement of the trocar 116 and the anvil 118 relative to the head assembly 114 from outside of the patient during use of the stapler 100. For example, the surgical stapler 100 may include a knob 152 that is attached to the handle 112 and coupled to the trocar 116. The knob 152 may be rotatably attached to the handle 112 such that the knob 152 is configured to rotate about the longitudinal axis of the handle 112. The knob 152 may be mechanically coupled to the trocar 116 such that rotation of the knob 152 in a first direction (e.g., counter-clockwise) causes the trocar 116 to move distally relative to the head assembly 114 and rotation of the knob 152 in an opposite second direction (e.g., clockwise) causes the trocar 116 to move proximally relative to the head assembly 114. Various types of components may be used to mechanically couple the knob 152 to the trocar 116 in this manner, such as one or more threaded members, geared members, cams, couplings, and/or other mechanical components. It will be appreciated that such components may be positioned within respective portions of the tubular shaft 110, the handle 112, and/or the head assembly 114.

The surgical stapler 100 also may include one or more components configured to allow the clinician to control movement of the staple pusher 130 and the circular knife 136 relative to the outer shell 122 and the staple guide 128 from outside of the patient during use of the stapler 100. For example, the surgical stapler 100 may include a lever 154 that is attached to the handle 112 and coupled to the staple pusher 130. The lever 154 may be pivotably attached to the handle 112 such that the lever 154 is configured to pivot relative to the handle 112. The lever 154 may be mechanically coupled to the staple pusher 130 such that pivotal movement of the lever 154 in a first direction (e.g., toward the handle 112) causes the staple pusher 130 to move distally relative to the outer shell 122 and the staple guide 128 and pivotal movement of the lever 154 in an opposite second direction (e.g., away from the handle 112) causes the staple pusher 130 to move proximally relative to the outer shell 122 and the staple guide 128. Various types of components may be used to mechanically couple the lever 154 to the staple pusher 130 in this manner, such as one or more threaded members, geared members, cams, couplings, and/or other mechanical components. It will be appreciated that such components may be positioned within respective portions of the tubular shaft 110, the handle 112, and/or the head assembly 114.

The insertion guide 120 may be formed as an elongated assembly configured for engaging the head assembly 114. As shown, the insertion guide 120 may include an expandable member 162, a tube 164, a port 166, and a distal tip 168. The expandable member 162 may be configured to move or be transitioned between a collapsed configuration, as shown in FIG. 1F, and an expanded configuration, as shown in FIGS. 1A and 1G. For example, the expandable member 162 may be configured to radially expand and collapse about the longitudinal axis of the expandable member 162 between the collapsed configuration and the expanded configuration. In some embodiments, as shown, the expandable member 162 may be an inflatable atraumatic balloon that is formed of a flexible, elastomeric material, e.g., silicone, polyurethane, etc. In this manner, the expandable member 162 may include an internal reservoir 170 that is configured to receive a fluid, such as air, water, or saline, to facilitate expansion of the expandable member 162 from the collapsed configuration to the expanded configuration. In some embodiments, the expandable member 162 expands by elastic deformation upon being filled with the fluid. As shown, the expandable member 162 may have a curved outer surface when the expandable member 162 is in the expanded configuration. In this manner, when the expandable member 162 is in the expanded configuration, the curved outer surface may facilitate insertion of the expandable member 162 into the patient and advancement of the expandable member 162 through surrounding anatomy and to a target location within the patient, without causing injury to the patient. According to various embodiments, the expandable member 162 may have a spherical shape, an egg shape, a toroidal shape, or other shape having a curved outer surface when the expandable member 162 is in the expanded configuration. It will be appreciated that the illustrated expandable member 162 is merely one example embodiment, and that other shapes and configurations of the expandable member 162 may be used with the surgical stapler 100.

The tube 164 of the insertion guide 120 may be formed as an elongated, hollow member extending from the proximal end of the expandable member 162. The tube 164 may be fixedly attached to the expandable member 162. In some embodiments, as shown, a distal portion of the tube 164 may be positioned within the expandable member 162. The tube 164 may include an internal lumen 172 that extends from the proximal end of the tube 164 toward the distal end of the tube 164 and is in fluid communication with the internal reservoir 170 of the expandable member 162. For example, the lumen 172 may terminate at an opening 174 that is defined in a sidewall of the tube 164 and provides fluid communication between the lumen 172 and the internal reservoir 170 of the expandable member 162. In this manner, a fluid may be delivered through the lumen 172 and into the internal reservoir 170 to facilitate expansion of the expandable member 162 from the collapsed configuration to the expanded configuration. Similarly, the fluid may be subsequently released from the internal reservoir 170 and through the lumen 172 to facilitate contraction of the expandable member 162 from the expanded configuration to the collapsed configuration. In some embodiments, the tube 164 may be formed of a flexible material configured to allow the shape of the tube 164 to be manipulated during use of the insertion guide 120. In other embodiments, the tube 164 may be formed of a rigid or substantially rigid material configured to maintain a predetermined shape of the tube 164 during use. It will be appreciated that the illustrated tube 164 is merely one example embodiment, and that other shapes and configurations of the tube 164 may be used with the surgical stapler 100.

The port 166 of the insertion guide 120 may be fixedly attached to the proximal end of the tube 164 and configured to facilitate attachment of a fluid delivery device, such as a syringe. In this manner, the fluid delivery device may be used to deliver the fluid through the tube 164 and into the expandable member 162 or to withdraw the fluid from the expandable member 162 and the tube 164. In some embodiments, the port 166 may include a luer lock connection or other type of connection for attaching the fluid delivery device thereto. It will be appreciated that the illustrated port 166 is merely one example embodiment, and that other shapes and configurations of the port 166 may be used with the surgical stapler 100.

The distal tip 168 of the insertion guide 120 may be formed as a non-expandable, elongated member extending from the distal end of the expandable member 162. The distal tip 168 may be fixedly attached to the expandable member 162. In some embodiments, as shown, a proximal portion of the distal tip 168 may be positioned within the expandable member 162. In some embodiments, the distal tip 168 may be hollow. In other embodiments, the distal tip 168 may be solid. In some embodiments, the distal tip 168 may be formed of a flexible material configured to allow the distal tip 168 to elastically deform as the distal tip 168 engages surrounding anatomy of the patient during use of the insertion guide 120. In other embodiments, the distal tip 168 may be formed of a rigid or substantially rigid material configured to maintain a predetermined shape of the distal tip 168 during use. It will be appreciated that the illustrated distal tip 168 is merely one example embodiment, and that other shapes and configurations of the distal tip 168 may be used with the surgical stapler 100. In some embodiments, the distal tip 168 may be omitted, such that the distal end of the expandable member 162 defines the distal end of the insertion guide 120.

In some embodiments, as shown in FIGS. 1F and 1G, the insertion guide 120 may be inserted through the head assembly 114 of the surgical stapler 100. In particular, the insertion guide 120 may be inserted through the head assembly 114 such that a distal portion of the insertion guide 120 extends distally beyond the distal end face 132 of the head assembly 114, a proximal portion of the insertion guide 120 extends proximally from the head assembly 114, and an intermediate portion of the insertion guide 120 is positioned within the head assembly 114. As shown in FIG. 1F, the insertion guide 120 may be advanced through the head assembly 114 while the expandable member 162 is in the collapsed configuration. Similarly, the insertion guide 120 may be removed from the head assembly 114 while the expandable member 162 is in the collapsed configuration. As described above, the insertion guide 120 may extend through the lateral opening 126 of the head assembly 114, through the central bore 124 of the head assembly 114, and distally beyond the distal end face 132 of the head assembly 114. In this manner, the insertion guide 120 also may extend through the central aperture of the staple guide 128, through the opening of the staple pusher 130, and through the central aperture of the circular knife 136. As shown, the head assembly 114 may have a first outer diameter OD1 and the expandable member 162 may have a second outer diameter OD2 when the expandable member 162 is in the collapsed configuration, with the second outer diameter OD2 being less than the first outer diameter OD1.

After inserting the insertion guide 120 through the head assembly 114, the expandable member 162 may be moved from the collapsed configuration to the expanded configuration, as shown in FIG. 1G. In some embodiments, the expandable member 162 may engage the distal end face 132 of the head assembly 114 when the expandable member 162 is in the expanded configuration. In some embodiments, a proximal portion of the expandable member 162 may be positioned within the central bore 124 of the head assembly 114 when the expandable member 162 is in the expanded configuration. In this manner, the proximal portion of the expandable member 162 may assist in self-centering the expandable member 162 relative to the longitudinal axis of the head assembly 114 when the expandable member 162 is moved from the collapsed configuration to the expanded configuration. In other embodiments, the entirety of the expandable member 162 may be positioned outside of the central bore 124 of the head assembly 114 and distally beyond the distal end face 132 when the expandable member 162 is in the expanded configuration. As shown, the expandable member 162 may have a third outer diameter OD3 when the expandable member 162 is in the expanded configuration. In some embodiments, the third outer diameter OD3 may be greater than the first outer diameter OD1 of the head assembly 114. In other embodiments, the third outer diameter OD3 may be equal to the first outer diameter OD1 of the head assembly 114.

In some embodiments, as shown in FIGS. 1H and 1I, the insertion guide 120 may be inserted through the tubular shaft 110 and the head assembly 114 of the surgical stapler 100. In particular, the insertion guide 120 may be inserted through the tubular shaft 110 and the head assembly 114 such that a distal portion of the insertion guide 120 extends distally beyond the distal end face 132 of the head assembly 114, a proximal portion of the insertion guide 120 extends proximally from the tubular shaft 110, and an intermediate portion of the insertion guide 120 is positioned within the tubular shaft 110 and the head assembly 114. In some embodiments, the insertion guide 120 may extend through the lumen of the tubular shaft 110 along with other internal components of the surgical stapler 100. In some embodiments, the tubular shaft 110 may include a dedicated tube, passage, or channel positioned within the lumen of the tubular shaft 110 and configured to receive the insertion guide 120 therethrough. In this manner, the tubular shaft 110 may have a predefined pathway for allowing the insertion guide 120 to extend therethrough and to shield the insertion guide 120 from other internal components within the tubular shaft 110. As shown in FIG. 1H, the insertion guide 120 may be advanced through the tubular shaft 110 and the head assembly 114 while the expandable member 162 is in the collapsed configuration. Similarly, the insertion guide 120 may be removed from the tubular shaft 110 and the head assembly 114 while the expandable member 162 is in the collapsed configuration. In some embodiments, the insertion guide 120 may extend through a lateral opening 126' of the handle 112, through a portion of the internal space of the handle 112, through the lumen of the tubular shaft 110, through the central bore 124 of the head assembly 114, and distally beyond the distal end face 132 of the head assembly 114. In this manner, the insertion guide 120 also may extend through the central aperture of the staple guide 128, through an opening of the staple pusher 130, and through the central aperture of the circular knife 136. As shown, the head assembly 114 may have a first outer diameter OD1 and the expandable member 162 may have a second outer diameter OD2 when the expandable member 162 is in the collapsed configuration, with the second outer diameter OD2 being less than the first outer diameter OD1.

After inserting the insertion guide 120 through the tubular shaft 110 and the head assembly 114, the expandable member 162 may be moved from the collapsed configuration to the expanded configuration, as shown in FIG. 1I. In some embodiments, the expandable member 162 may engage the distal end face 132 of the head assembly 114 when the expandable member 162 is in the expanded configuration. In some embodiments, a proximal portion of the expandable member 162 may be positioned within the central bore 124 of the head assembly 114 when the expandable member 162 is in the expanded configuration. In this manner, the proximal portion of the expandable member 162 may assist in self-centering the expandable member 162 relative to the longitudinal axis of the head assembly 114 when the expandable member 162 is moved from the collapsed configuration to the expanded configuration. In other embodiments, the entirety of the expandable member 162 may be positioned outside of the central bore 124 of the head assembly 114 and distally beyond the distal end face 132 when the expandable member 162 is in the expanded configuration. As shown, the expandable member 162 may have a third outer diameter OD3 when the expandable member 162 is in the expanded configuration. In some embodiments, the third outer diameter OD3 may be greater than the first outer diameter OD1 of the head assembly 114. In other embodiments, the third outer diameter OD3 may be equal to the first outer diameter OD1 of the head assembly 114.

In some embodiments, the surgical stapler 100 may include both the lateral opening 126 of the head assembly 114 and the lateral opening 126' of the handle 112, as shown in FIG. 1A. In this manner, the clinician may have the option of using the lateral opening 126 of the head assembly 114 to extend the insertion guide 120 through only the head assembly 114, as described above with respect to FIGS. 1F and 1G, or using the lateral opening 126' of the handle 112 to extend the insertion guide 120 through both the tubular shaft 110 and the head assembly 114, as described above with respect to FIGS. 1H and 1I. In other embodiments, the lateral opening 126 of the head assembly 114 or the lateral opening 126' of the handle 112 may be omitted.

Methods of Use

Figure 2C:
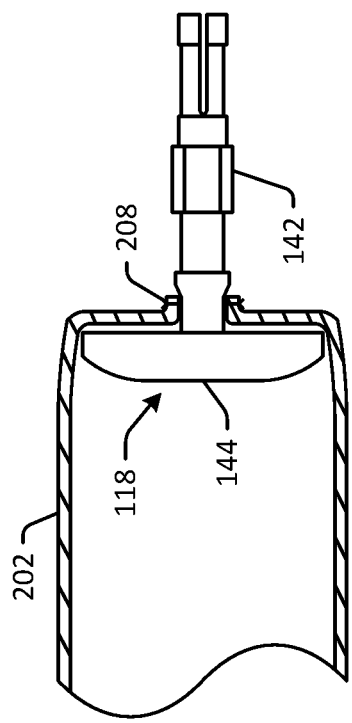
Figure 2C:
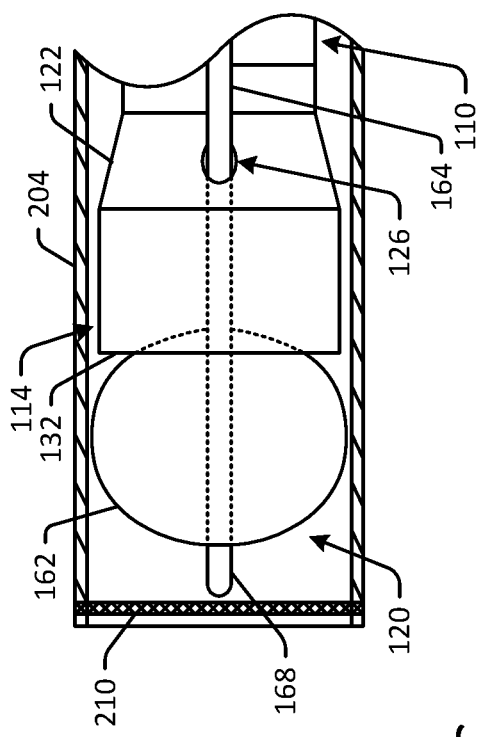

FIGS. 2A-2H illustrate an example method of using the surgical stapler 100 to perform an end-to-end anastomosis between two tissue segments of a tubular tissue structure of a patient, in accordance with one or more embodiments of the disclosure. FIG. 2A shows a tubular tissue structure 200 of a patient, which includes a first tissue segment 202, a second tissue segment 204, and an intermediate portion 206 of the tubular tissue structure 200 to be removed from the patient. In some embodiments, the tubular tissue structure 200 may be a colon of the patient, the first tissue segment 202 may be an upper colon segment, and the second tissue segment 204 may be a lower colon segment. Following resection of the intermediate portion 206, the first tissue segment 202 and the second tissue segment 204 may need to be reconnected to one another by performing an end-to-end anastomosis to restore the natural function of the tubular tissue structure 200.

The anastomosis procedure may begin by inserting the anvil head 144 of the anvil 118 into the first tissue segment 202 and securing the free end of the first tissue segment 202 around the anvil shaft 142 of the anvil 118, as shown in FIG. 2B. In this manner, the anvil shaft 142 may extend outside of the first tissue segment 202, while the anvil head 144 is maintained within the first tissue segment 202. In some embodiments, the free end of the first tissue segment 202 may be secured around the anvil shaft 142 by suturing the tissue, for example, to form a purse-string suture 208. Meanwhile, the free end of the second tissue segment 204 may be closed by suturing the tissue, for example, to form a linear suture 210, as shown in FIG. 2B.

After closing the free end of the second tissue segment 204, the head assembly 114 of the surgical stapler 100 may be inserted into the patient and advanced toward the closed end of the second tissue segment 204. As described above, the insertion guide 120 may be used to facilitate insertion of the head assembly 114 and advancement of the head assembly 114 to the closed end of the second tissue segment 204. In particular, the insertion guide 120 may be inserted through the head assembly 114, as described above with respect to FIG. 1F, and the expandable member 162 may be moved from the collapsed configuration to the expanded configuration, as described above with respect to FIG. 1G. Alternatively, the insertion guide 120 may be inserted through the tubular shaft 110 and the head assembly 114, as described above with respect to FIG. 1H, and the expandable member 162 may be moved from the collapsed configuration to the expanded configuration, as described above with respect to FIG. 1I. For example, the expandable member 162 may be expanded to the expanded configuration by delivering a fluid through the tube 164 and into the internal reservoir 170 of the expandable member 162 via a fluid delivery device attached to the port 166. The insertion guide 120 and the head assembly 114 then may be inserted into the patient and advanced through the surrounding anatomy until the expandable member 162 and the head assembly 114 are positioned adjacent to the closed end of the second tissue segment 204, as shown in FIG. 2C. Meanwhile, the port 166 and the fluid delivery device may remain positioned outside of the patient. In embodiments in which the tubular tissue structure 200 is the colon of the patient and the second tissue segment 204 is the lower colon segment, the expandable member 162 may ease insertion of the head assembly 114 through the anus, through the contours of the rectum, and through the lower colon segment, while inhibiting the distal end face 132 of the head assembly 114 from engaging the surrounding anatomy.

Figure 2D:
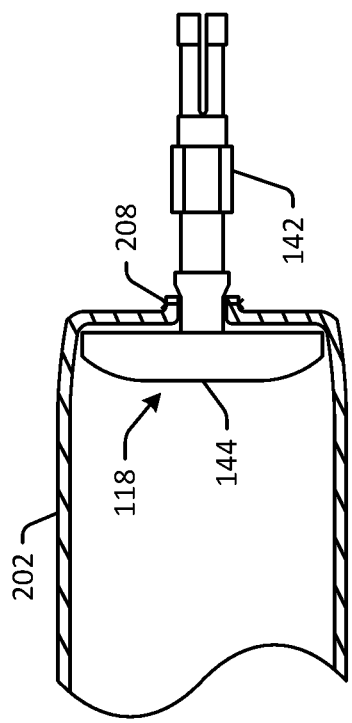
Figure 2D:
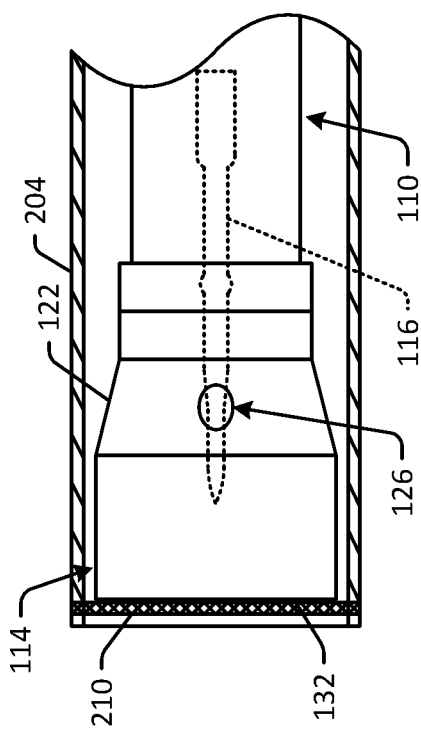

After the expandable member 162 and the head assembly 114 are positioned adjacent to the closed end of the second tissue segment 204, the expandable member 162 may be moved from the expanded configuration to the collapsed configuration. For example, the fluid delivery device may be used to withdraw the fluid from the internal reservoir 170 of the expandable member 162, thereby causing the expandable member 162 to assume the collapsed configuration. The insertion guide 120 then may be withdrawn proximally from the head assembly 114 and removed from the patient. After removal of the insertion guide 120 from the head assembly 114, the head assembly 114 may be further advanced to a position adjacent to the closed end of the second tissue segment 204, as shown in FIG. 2D.

Figure 2E:
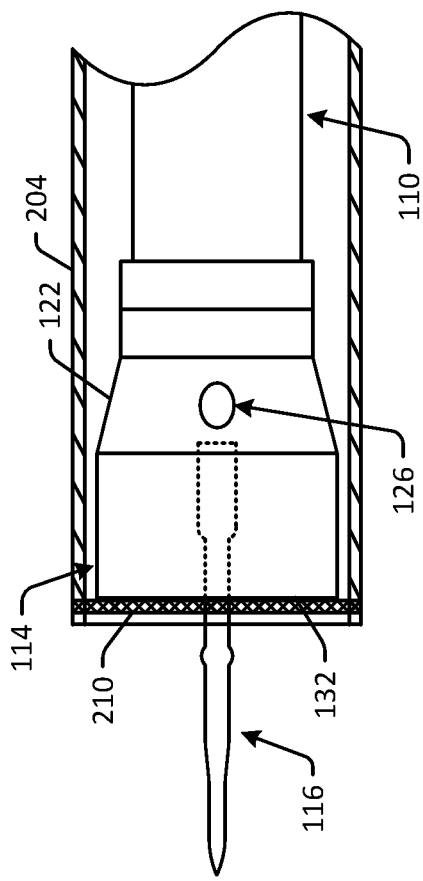
Figure 2E:
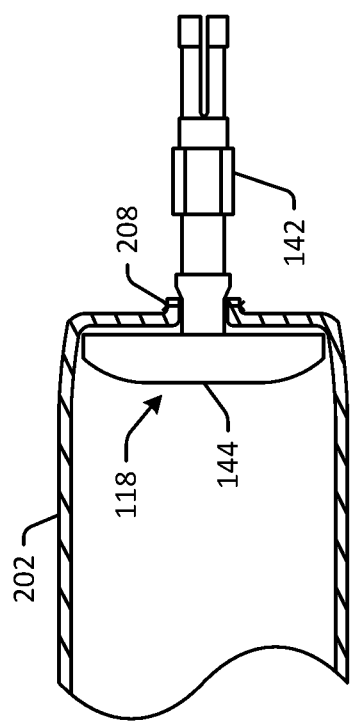

With the head assembly 114 positioned adjacent to the closed end of the second tissue segment 204, the trocar 116 may be passed through the closed end of the second tissue segment 204, as shown in FIG. 2E. For example, the knob 152 of the surgical stapler 100 may be rotated counterclockwise to cause the trocar 116 to move from the retracted position to the extended position. In this manner, the trocar 116 may be advanced through the closed end of the second tissue segment 204 and extend into the space between the first tissue segment 202 and the second tissue segment 204.

Figure 2F:
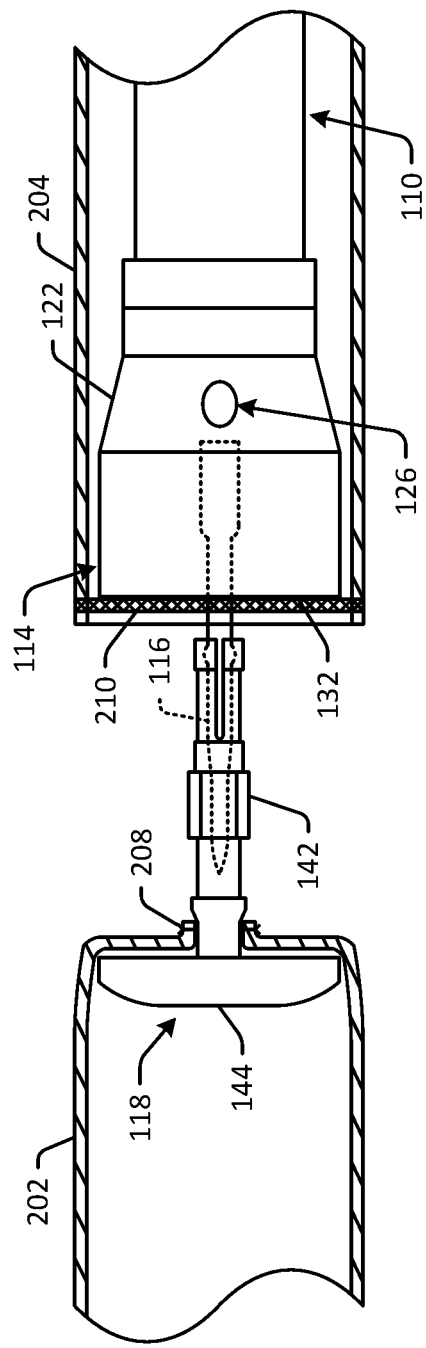

The anvil 118 and the trocar 116 then may be attached to one another, as shown in FIG. 2F. For example, the anvil 118 and/or the trocar 116 may be grasped via one or more surgical instruments, such as forceps, and moved relative to one another such that the anvil 118 is advanced over the trocar 116 and secured thereto by the connection between the protrusion 140 and the groove 148.

Figure 2G:
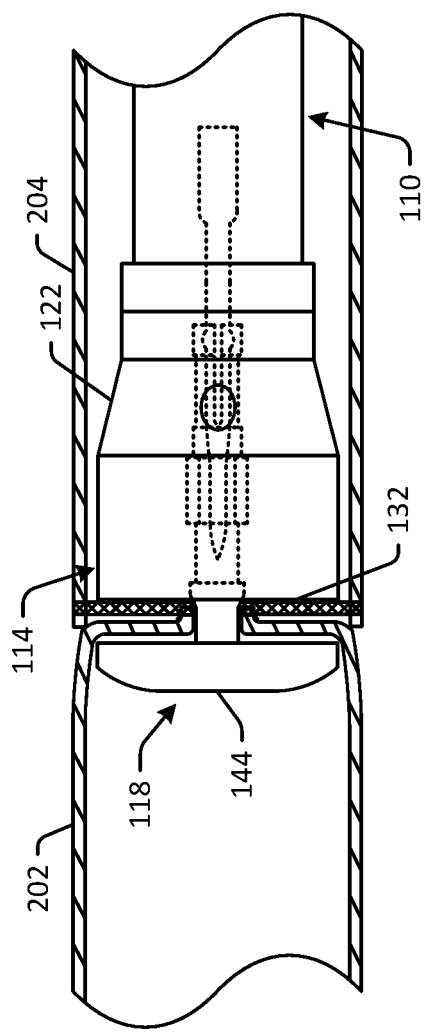
Figure 2H:
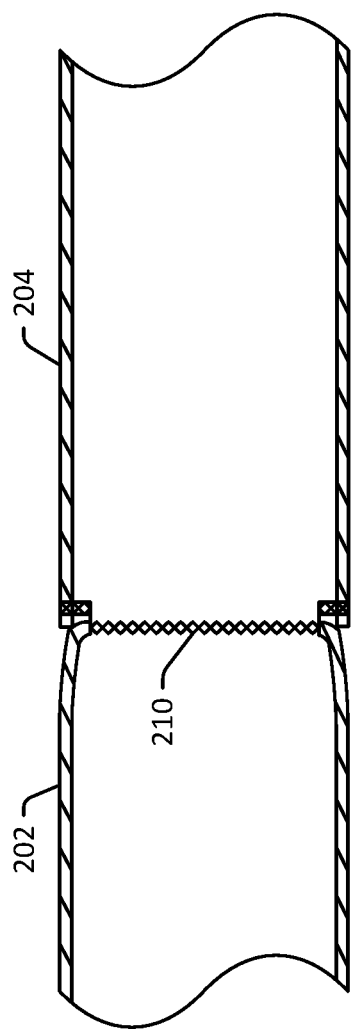

After attaching the anvil 118 to the trocar 116, the anvil 118 and the trocar 116 may be moved from the extended position to the retracted position, as shown in FIG. 2G. For example, the knob 152 of the surgical stapler 100 may be rotated clockwise to cause the trocar 116 and the anvil 118 to move from the extended position to the retracted position. In this manner, the respective ends of the first tissue segment 202 and the second tissue segment 204 may be drawn together and captured between the anvil head 144 and the distal end face 132 of the head assembly 114. The head assembly 114 then may be actuated to facilitate formation of a circular array of staples through the respective end portions of the first tissue segment 202 and the second tissue segment 204 and to core respective inner portions of the first tissue segment 202 and the second tissue segment 204. For example, the lever 154 of the surgical stapler 100 may be moved relative to the handle 112 to actuate the head assembly 114. The actuation of the head assembly 114 may cause the staple pusher 130 and the circular knife 136 to move distally relative to the outer shell 122 and the staple guide 128. As described above, the movement of the staple pusher 130 may cause the staples to be ejected from the staple guide 128, advanced through the respective end portions of the first tissue segment 202 and the second tissue segment 204, and deformed against the anvil head 144. In this manner, a circular array of staples 212 may be formed to reconnect the first tissue segment 202 and the second tissue segment 204. Meanwhile, the movement of the circular knife 136 may cause the cutting edge thereof to cut the respective inner portions of the first tissue segment 202 and the second tissue segment 204 against the anvil head 144. In this manner, fluid communication between the first tissue segment 202 and the second tissue segment 204 may be restored. After actuating the head assembly 114, the surgical stapler 100 may be removed from the patient, leaving the first tissue segment 202 and the second tissue segment 204 reconnected by an end-to-end anastomosis, as shown in FIG. 2H.

Modifications and variations of the devices, systems, and methods described herein will be obvious to those skilled in the art from the foregoing detailed description. Such modifications and variations are intended to come within the scope of the appended claims.

I claim:

1. A surgical stapler comprising:
   a tubular shaft having a proximal end and a distal end;
   a handle extending from the proximal end of the tubular shaft;
   a head assembly extending from the distal end of the tubular shaft; and
   an insertion guide configured to removably extend through the head assembly, the insertion guide comprising an inflatable member configured to move between a deflated configuration and an inflated configuration, in which the inflatable member is configured to facilitate introduction of the head assembly into a patient's colon,
   wherein the head assembly is configured to receive an anvil,
   wherein the head assembly comprises staples to be pressed against the anvil during stapling with the surgical stapler,
   wherein the head assembly comprises a distal end face, and
   wherein the insertion guide is configured to extend distally beyond the distal end face of the head assembly; wherein the head assembly comprises an outer shell comprising a central bore defined therein, and wherein the insertion guide is configured to extend at least partially through the central bore; wherein the outer shell further comprises a lateral opening defined in an outer surface of the outer shell and in communication with the central bore, and wherein the insertion guide is configured to extend through the lateral opening and into the central bore.

2. The surgical stapler of claim 1, wherein the inflatable member is configured to engage the distal end face of the head assembly when the inflatable member is in the inflated configuration, and wherein the inflatable member is configured to be spaced apart from the distal end face of the head assembly when the inflatable member is in the deflated configuration.

3. The surgical stapler of claim 1, wherein the head assembly further comprises a staple guide positioned within the central bore, and wherein the insertion guide is configured to extend through a central aperture of the staple guide.

4. The surgical stapler of claim 1, wherein the head assembly further comprises a circular knife positioned within the central bore, and wherein the insertion guide is configured to extend through a central aperture of the circular knife.

5. The surgical stapler of claim 1, wherein the inflatable member is configured to be positioned at least partially within the central bore when the inflatable member is in the inflated configuration, and wherein the inflatable member is configured to be withdrawn from the central bore when the inflatable member is in the deflated configuration.

6. The surgical stapler of claim 1, wherein the head assembly has a first outer diameter, wherein the inflatable member has a second outer diameter when the inflatable member is in the deflated configuration, wherein the inflatable member has a third outer diameter when the inflatable member is in the deflated configuration, wherein the second outer diameter is less than the first outer diameter, and wherein the third outer diameter is equal to or greater than the first outer diameter.

7. The surgical stapler of claim 1, wherein the inflatable member comprises a balloon configured to radially collapse and expand to move the inflatable member between the deflated configuration and the inflated configuration.

8. The surgical stapler of claim 7, wherein the insertion guide further comprises:
a tube extending from a proximal end of the inflatable member and in fluid communication with an internal reservoir of the balloon; and
a port attached to a proximal end of the tube and configured to attach to a fluid delivery device.

9. The surgical stapler of claim 1, wherein the insertion guide is configured to extend through the tubular shaft and the head assembly.

10. A surgical stapler comprising:
a tubular shaft having a proximal end and a distal end;
a handle extending from the proximal end of the tubular shaft;
a head assembly extending from the distal end of the tubular shaft; and
an insertion guide configured to removably extend through the head assembly and being completely removable from the head assembly, the insertion guide comprising:
a balloon configured to move between a collapsed configuration and an expanded configuration; and
a tube extending from a proximal end of the balloon and in fluid communication with an internal reservoir of the balloon,
wherein the head assembly is configured to receive an anvil,
wherein the head assembly comprises staples to be pressed against the anvil during stapling with the surgical stapler; wherein the head assembly comprises an outer shell comprising a central bore defined therein, and wherein the insertion guide is configured to extend at least partially through the central bore; wherein the outer shell further comprises a lateral opening defined in an outer surface of the outer shell and in communication with the central bore, and wherein the insertion guide is configured to extend through the lateral opening and into the central bore.

11. The surgical stapler of claim 10, wherein the head assembly comprises a distal end face, wherein the insertion guide is configured to extend distally beyond the distal end face, wherein the balloon is configured to be spaced apart from the distal end face when the balloon is in the collapsed configuration, and wherein the balloon is configured to engage the distal end face when the balloon is in the expanded configuration.

12. The surgical stapler of claim 10, wherein the head assembly comprises:
a central bore defined therein;
a staple guide positioned within the central bore; and
a circular knife positioned within the central bore;
wherein the insertion guide is configured to extend at least partially through the central bore, and wherein the insertion guide is configured to extend through a central aperture of the staple guide and a central aperture of the circular knife.

13. A method of introducing a surgical stapler into a patient, the method comprising:
advancing an insertion guide through a head assembly of the surgical stapler, such that the insertion guide extends distally beyond a distal end face of the head assembly;
moving an inflatable member of the insertion guide from a deflated configuration and an inflated configuration;
inserting the inflatable member and the head assembly into a tubular tissue structure of the patient while the inflatable member is in the inflated configuration such that the head assembly is positioned ready to receive an anvil;
advancing the inflatable member and the head assembly through the tubular tissue structure to a target location;
moving the inflatable member from the inflated configuration to the deflated configuration while the inflatable member is at the target location; and then
removing the insertion guide from the head assembly,
wherein the head assembly comprises staples to be pressed against the anvil during stapling with the surgical stapler.

14. The method of claim 13, wherein the surgical stapler further comprises a tubular shaft extending from a proximal end of the head assembly, and wherein the method further comprises advancing the insertion guide through the tubular shaft.

15. The method of claim 13, wherein the inflatable member comprises a balloon, and wherein moving the inflatable member from the deflated configuration to the-inflated configuration comprises inflating the balloon.

16. The method of claim 13, wherein the tubular tissue structure comprises a segment of a colon of the patient.

17. A kit of parts, comprising:
a surgical stapler which comprises:
a tubular shaft having a proximal end and a distal end,
a handle extending from the proximal end of the tubular shaft, and
a head assembly extending from the distal end of the tubular shaft, wherein the head assembly comprises a central bore defined therein, a distal end face, and a staple guide positioned within the central bore; and
an insertion guide which comprises:
a balloon configured to move between a collapsed configuration and an expanded configuration, and
a tube extending from a proximal end of the balloon and in fluid communication with an internal reservoir of the balloon, wherein the head assembly is configured to receive the insertion guide such that (i) the insertion guide is removably extendible through the head assembly and (ii) the balloon is configured to extend distally beyond the distal end face of the head assembly when the balloon is in the expanded configuration; wherein the head assembly comprises an outer shell comprising a central bore defined therein, and wherein the insertion guide is configured to extend at least partially through the central bore; wherein the outer shell further comprises a lateral opening defined in an outer surface of the outer shell and in communication with the central bore, and wherein the insertion guide is configured to extend through the lateral opening and into the central bore.

18. The kit of claim 17, further comprising an anvil configured to be received by the head assembly.

\* \* \* \* \*